US006810283B2

(12) United States Patent
Suribhotla et al.

(10) Patent No.: US 6,810,283 B2
(45) Date of Patent: Oct. 26, 2004

(54) MULTIPLE TEMPLATES FOR FILTERING OF FAR FIELD R-WAVES

(75) Inventors: Rajasekhar V. Suribhotla, North Royalton, OH (US); David K. L. Peterson, Saugus, CA (US); Girard B. Borgerding, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 414 days.

(21) Appl. No.: 09/951,320

(22) Filed: Sep. 13, 2001

(65) Prior Publication Data

US 2003/0050563 A1 Mar. 13, 2003

(51) Int. Cl.[7] .............................................. A61B 5/0428
(52) U.S. Cl. ...................................................... 600/509
(58) Field of Search ................................ 600/509–510, 600/515, 518, 521; 607/4–5, 9, 14, 25–26

(56) References Cited

U.S. PATENT DOCUMENTS

| | | | |
|---|---|---|---|
| 4,721,114 A | * | 1/1988 | DuFault et al. .............. 600/509 |
| 4,799,486 A | | 1/1989 | DuFault |
| 4,799,493 A | | 1/1989 | DuFault |
| 4,825,870 A | | 5/1989 | Mann et al. |
| 5,086,772 A | | 2/1992 | Larnard et al. |
| 5,117,824 A | | 6/1992 | Keimel et al. |
| 5,312,445 A | | 5/1994 | Nappholz et al. |
| 5,447,519 A | | 9/1995 | Peterson |
| 5,755,739 A | | 5/1998 | Sun et al. |
| 5,759,196 A | | 6/1998 | Hess et al. |
| 5,778,881 A | | 7/1998 | Sun et al. |
| 5,782,888 A | | 7/1998 | Sun et al. |
| 5,814,083 A | | 9/1998 | Hess et al. |
| 5,817,133 A | | 10/1998 | Houben |
| 5,885,221 A | * | 3/1999 | Hsu et al. .................... 600/515 |
| 6,032,072 A | | 2/2000 | Greenwald et al. |

OTHER PUBLICATIONS

Theres, Heinz, "P Wave and Far–Field R Wave Detection in Pacemaker Patient Atrial Electrograms", *PACE*, vol. 23, Apr. 2000, Part I, pp. 434–440.

Greenhut, et al., Detection of Atrial Activation By Intraventricular Electrogram Morphology Analysis: A Study to Determine the Feasibility of P Wave Synchronous Pacing From a Standard Ventricular Lead, PACE, vol. 16, pp. 1293–1303 (1993).

DuFault, et al., "Dual Lead Fibrillation Detection for Implantable Defibrillators via LMS Algorithm," IEEE Comp. Cardiol., pp. 163–166 (1987).

Widrow et al., "Adaptive Noise Canceling: Principles and Applications," IEEE Proc., vol. 68, No. 12, pp. 1692–1716 (1975).

DuFault, et al., "P–Wave Detection in the Surface ECG via the LMS Algorithm," IEEE Comp. Cardiol., pp. 245–248 (1987).

Sahakian, et al., "Canceling the Cardiogenic Artifact in Impedence Pneumography," IEEE $17^{th}$ ACEMB, pp. 855–859 (1985).

Yi–Sheng et al., "P–Wave Detection by an Adaptive QRS–T Cancellation Technique," IEEE Comp. Cardiol., pp. 249–252 (1986).

* cited by examiner

Primary Examiner—Kennedy Schaetzle
Assistant Examiner—Kristen Droesch
(74) Attorney, Agent, or Firm—Michael C. Soldner; Girma Wolde-Michael

(57) ABSTRACT

The invention presents techniques for processing an atrial electrogram. An atrial electrogram senses atrial events, but may also sense a ventricular event, causing a far field R-wave to be present in the atrial electrogram signal. A far field R-wave is an undesired artifact. The invention provides techniques for estimating the far field R-wave and subtracting the far field R-wave from the atrial electrogram signal.

25 Claims, 6 Drawing Sheets

MULTIPLE TEMPLATES FOR FILTERING OF FAR FIELD R-WAVES

FIELD

The invention relates to automated discrimination of cardiac events, and in particular, to cardiac events detected by an atrial electrogram (A-EGM).

BACKGROUND

In the medical fields of cardiology and electrophysiology, many tools are used to assess the condition and function of a patient's heart from observed frequency, polarity and amplitudes of the PQRST complex associated with a heart cycle. One such tool is the electrogram (EGM), which is a form of an implantable cardiac monitor. An EGM may be included in devices such as a cardiac pacemaker, a pacemaker/cardioverter/defibrillator (PCD) or an implantable cardioverter/defibrillator (ICD).

An EGM that records the activity of an atrium of the heart is called an atrial EGM, or A-EGM. An A-EGM may detect arrhythmia in the atrium, such as bradycardia and tachyarrhythmia. Events detected by an A-EGM may be converted to electrical signals, which may be used in many ways. The signals may be relayed by telemetry to medical personnel for analysis and diagnosis, for example. The signals may be used for treatment by an implantable device, which has been programmed to detect and respond to a particular arrhythmia.

An A-EGM may also be used in concert with a ventricular EGM, or V-EGM. Medical personnel and implantable devices may use both A-EGM and V-EGM signals for diagnosis and treatment.

In diagnosis and treatment, it is important that the A-EGM provide a true representation of the atrial electrical activity. The A-EGM may, however, detect some ventricular electrical activity. In particular, an A-EGM may detect an R-wave associated with ventricular depolarization. An atrial sensing of ventricular depolarization is called a far field R-wave.

Ordinarily, the sense threshold of an A-EGM may be set lower than the sense threshold of a V-EGM. This is because the P-wave amplitude, which represents atrial depolarization, is significantly lower than that of the R-wave, which represents ventricular depolarization. Because an A-EGM is more sensitive than a V-EGM, an R-wave, whether intrinsic or triggered by a ventricular pace, may often be detected by an A-EGM. The R-wave detected by the A-EGM may have an amplitude exceeding the P-wave sense threshold.

Far field R-waves that are detected in A-EGM signals may lead to misinterpretation of atrial rhythms. In particular, a far field R-wave may suggest an event in the atrium, when in fact the far field R-wave results from a ventricular event. Sensing an R-wave in an A-EGM signal and mistaking the sensed signal for an atrial event is called "oversensing." Misinterpretation of atrial rhythms may in turn lead to an incorrect diagnosis and/or inappropriate treatment.

Several techniques have been put forward for rejecting far field R-waves and/or discriminating P-waves from far field R-waves. For example, U.S. Pat. No. 4,799,486 to DuFault describes a method and apparatus for suppressing the ventricular component of a signal detected by an atrial sensing lead, using an adaptive filter that employs the Widrow-Hoff least mean square algorithm. U.S. Pat. No. 4,799,493 to DeFault describes a tachyarrhythmia/fibrillation detector that employs the Widrow-Hoff least mean square algorithm to estimate a transfer function.

U.S. Pat. No. 4,825,870 to Mann et al. describes circuitry to detect and compensate for "crosstalk," which is defined a signal originating in one chamber of the heart being sensed by circuits designed to sense signals in the other chamber of the heart. If crosstalk occurs, a shortened atrio-ventricular (AV) delay is triggered.

U.S. Pat. No. 5,755,739 to Sun et al. illustrates methods and apparatus for discriminating atrial P-waves from ventricular events such as far field R-waves. The A-EGM signal is filtered with an adaptive filter and is subjected to a morphological analysis with respect to a morphological model of a P-wave called a "P-wave template."

U.S. Pat. No. 5,759,196 to Hess et al. describes techniques for sensing far field R-waves and using the sensed far field R-waves to determine the presence of atrial tachyarrhythmia.

U.S. Pat. No. 5,778,881 to Sun et al. and U.S. Pat. No. 5,782,888 to Sun et al. describes the use of Hidden Markov Modeling techniques with wavelet transforms to discriminate cardiac events of interest in EGM signals. These techniques may be employed in connection with far field R-waves in A-EGM signals.

U.S. Pat. No. 5,814,083 to Hess et al. sets forth implementation of an algorithm that used sensed far field R-waves to determine whether to search for blocked 2:1 sensing.

U.S. Pat. No. 5,817,133 to Houben presents techniques for morphological filtering to eliminate far field R-waves from A-EGM signals. The morphological filtering employs morphological operations such as dilation and erosion operations and open and close operations.

Each of the above patents is incorporated herein in their respective entireties.

SUMMARY

The invention is directed to techniques for filtering far field R-waves from A-EGM signals, resulting in accurate interpretation of atrial rhythms and delivery of appropriate therapies. Based upon the nature, rate and timing of atrio-ventricular events, a morphological model of an estimated far field R-wave or "template" is selected from a plurality of templates. The estimated far field R-wave is then subtracted from the A-EGM signal, which includes the undesirable far field R-wave.

The difference is a filtered A-EGM signal in which the far field R-wave is attenuated. This filtered signal is indicative of atrial activity, and may be compared to a P-wave sense threshold. The risk that a far field R-wave will be mistaken for a P-wave is substantially reduced.

In one embodiment, the invention provides a method comprising receiving an A-EGM signal, selecting an estimated far field R-wave for a cardiac cycle from a plurality of estimated far field R-waves and subtracting the selected estimated far field R-wave from the A-EGM signal for the cardiac cycle. The selected estimated far field R-wave may be a function of cardiac events. The method may include, for example, selecting an estimated far field R-wave associated with a premature ventricular contraction when a premature ventricular contraction is sensed, or selecting an estimated far field R-wave associated with a ventricular pace when the patient receives a ventricular pace.

In another embodiment, the invention provides a device comprising an atrial lead and a filter that selects an estimated far field R-wave from a plurality of estimated far field R-waves and subtracts the selected estimated far field R-wave from an atrial electrogram signal received from the atrial lead. The plurality of estimated far field R-waves may be stored in memory in the device. The device may further include a comparator that compares the filtered atrial electrogram signal to a pre-selected atrial sense threshold and generates an atrial sense signal when the filtered atrial electrogram signal exceeds the atrial sense threshold.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

Figure 1:
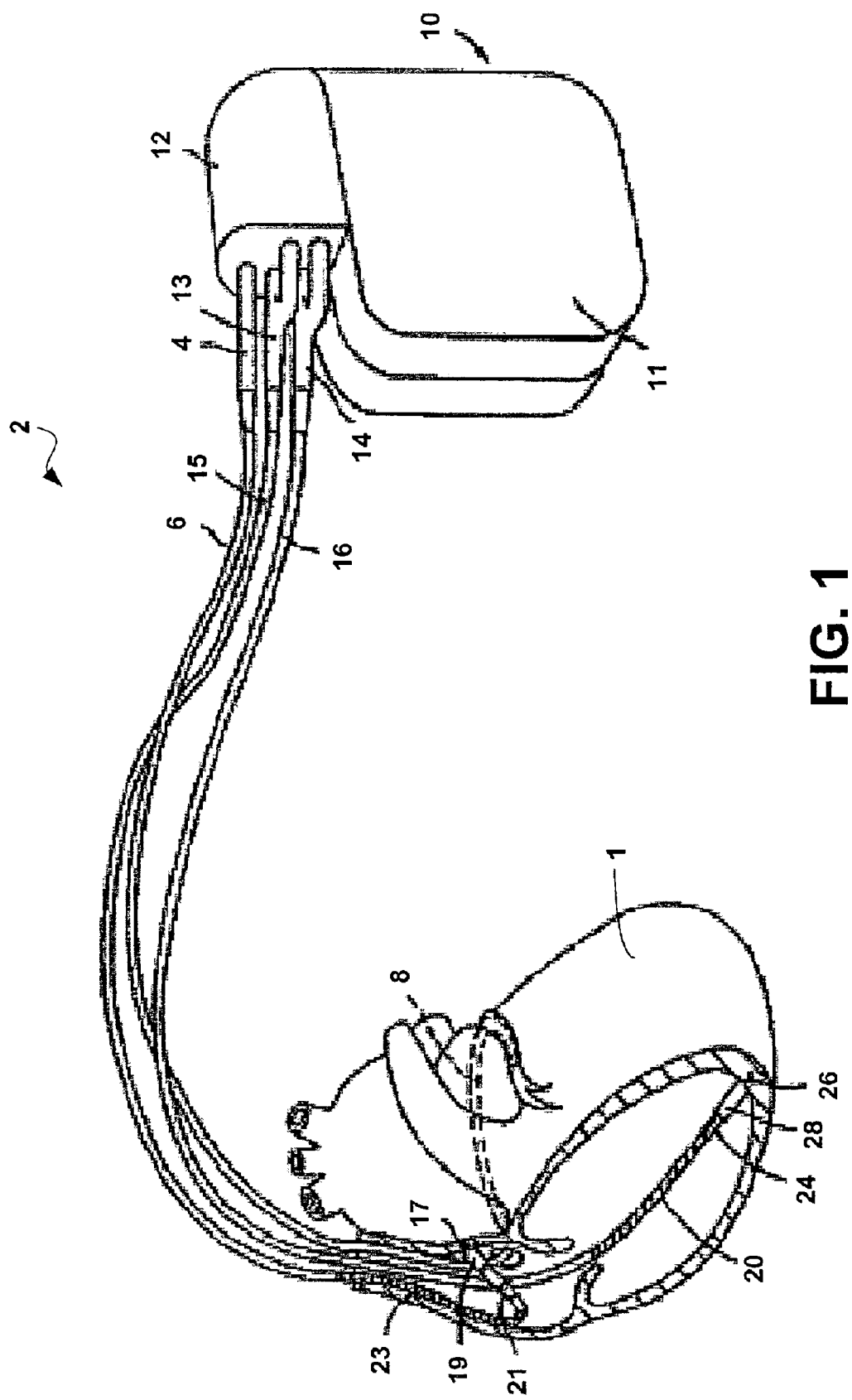
FIG. 1 is a diagram illustrating an implantable defibrillator and lead system.

FIG. 1 illustrates an implantable defibrillator and lead system 2 in which the present invention may be practiced. System 2 is shown in association with human heart 1. The invention is not limited to the exemplary device or system shown in FIG. 1, but may be practiced in a wide variety of device implementations, such as a pacemaker or an ICD. Other techniques or therapies responsive to A-EGM signals, such as therapies that administer drugs in response to atrial tachyarrhythmia, also may practice the invention.

System 2 comprises a ventricular lead, which includes elongated insulative lead body 16, carrying three concentric coiled conductors separated from one another by tubular insulative sheaths. Located adjacent the distal end of the ventricular lead are ring electrode 24, extendable helix electrode 26, mounted retractably within insulative electrode head 28, and elongated (approximately 5 cm) defibrillation coil electrode 20. Defibrillation electrode 20 may be fabricated from many materials, such as platinum or platinum alloy. Each of the electrodes is coupled to one of the coiled conductors within lead body 16.

Electrodes 24 and 26 are employed for cardiac pacing and for sensing ventricular depolarizations. Accordingly, electrodes 24 and 26 serve as sensors for a V-EGM. At the proximal end of the ventricular lead is bifurcated connector 14 that carries three electrical connectors, each coupled to one of the coiled conductors.

The atrial/superior vena cava (SVC) lead includes elongated insulative lead body 15, carrying three concentric coiled conductors, separated from one another by tubular insulative sheaths, corresponding to the structure of the ventricular lead. Located adjacent the distal end of the atrial/SVC lead are ring electrode 21 and extendable helix electrode 17, mounted retractably within insulative electrode head 19. Each of the electrodes is coupled to one of the coiled conductors within lead body 15. Electrodes 17 and 21 are employed for atrial pacing and for sensing atrial depolarizations. Accordingly, electrodes 17 and 21 serve as sensors for an A-EGM.

In addition to detecting atrial activity, electrodes 17 and 21 may detect far field R-waves, which are caused by ventricular activity. The extent to which ventricular events are detected by atrial electrodes 17 and 21 is a function of several factors, including the placement of the electrodes within heart 1. In some patients, atrial electrodes 17 and 21 do not detect ventricular events at all. In other patients, the A-EGM signal may include a prominent far field R-wave.

Elongated coil electrode 23 is provided proximal to electrode 21 and coupled to the third conductor within the lead body 15. Electrode 23 preferably is 10 cm in length or greater and is configured to extend from the SVC toward the tricuspid valve. At the proximal end of the lead is a bifurcated connector 13 which carries three electrical connectors, each coupled to one of the coiled conductors.

The coronary sinus lead includes elongated insulative lead body 6, carrying one coiled conductor, coupled to elongated (approximately 5 cm) coiled defibrillation electrode 8. Electrode 8, illustrated in broken outline, is located within the coronary sinus and great vein of heart 1. At the proximal end of the coronary sinus lead is connector plug 4, which carries an electrical connector coupled to the coiled conductor.

Implantable PCD 10 is shown in combination with the leads, with the lead connector assemblies 4, 13 and 14 inserted into connector block 12. Optionally, insulation of the outward facing portion of the housing 11 of the PCD 10 may be provided using a plastic coating, e.g., parylene or silicone rubber, as is employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles.

Electrical stimulation may be indicated when the implantable device detects arrhythmia. It is therefore important to recognize when the patient is experiencing an arrhythmia. When an A-EGM signal discloses the presence of a P-wave and a far-field R-wave, oversensing may occur. The far field R-wave may be mistaken for a P-wave, possibly leading to an incorrect diagnosis of arrhythmia and inappropriate stimulation.

Figure 2:
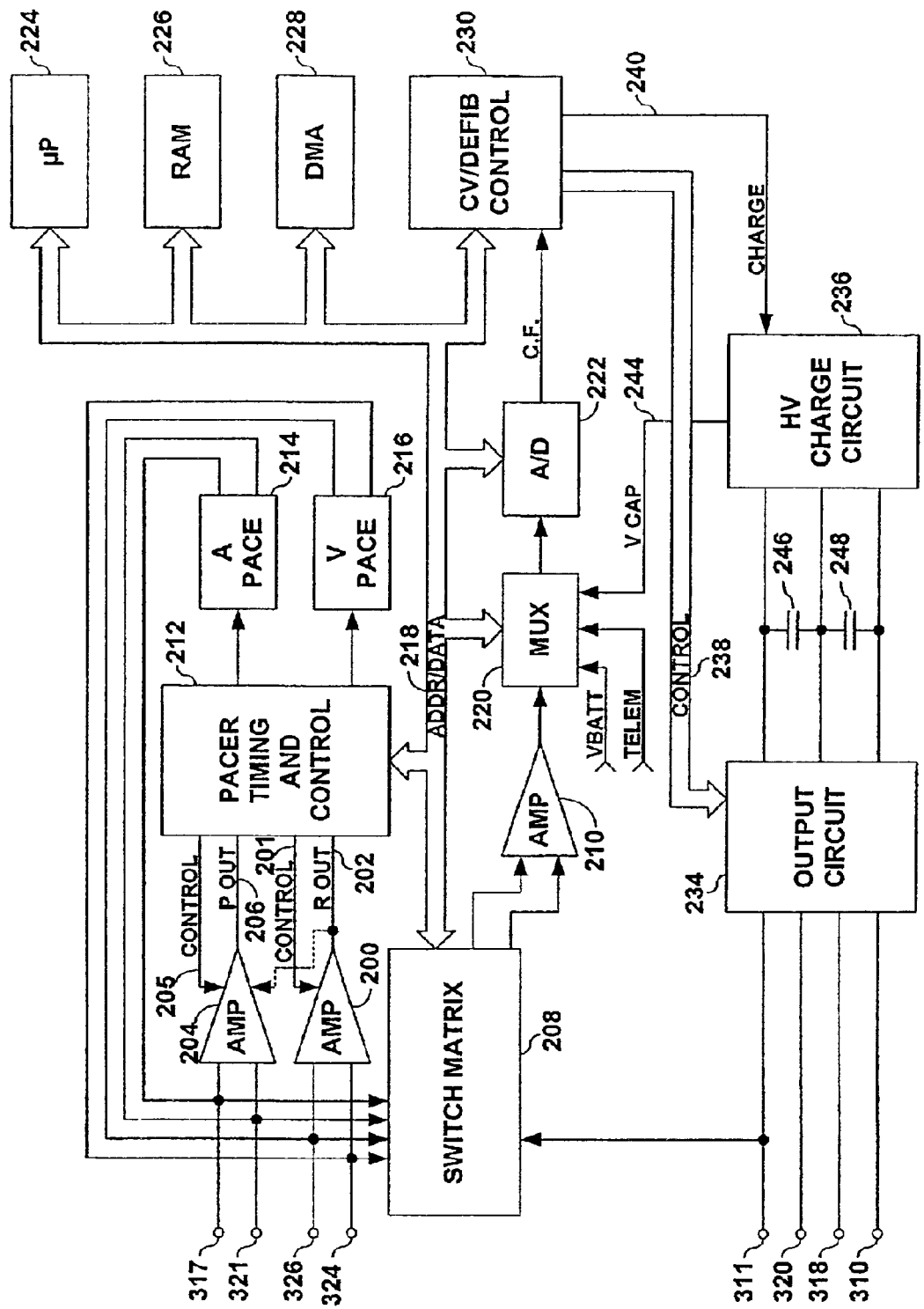
FIG. 2 is a functional schematic diagram of an implantable PCD.

FIG. 2 is a functional schematic diagram of an implantable PCD. The diagram illustrates, among other things, how diagnosis of arrhythmias and treatment of arrhythmias are related.

The implantable PCD shown in FIG. 2 is a device in which the present invention may be practiced. FIG. 2 should be taken as exemplary of one type of device in which the invention may be embodied. The invention is not limited to the exemplary device shown in FIG. 2, but may be practiced in a wide variety of device implementations, such as an a pacemaker or an ICD.

FIG. 2 is one possible functional representation of system 2 shown in FIG. 1. The representation put forth in FIG. 2 is not limited to system 2 shown in FIG. 1, however, and the invention is not limited to the representation shown in FIG. 2. The invention may be practiced in a system that includes more or fewer features than are depicted in FIG. 2.

The device illustrated in FIG. 2 is provided with an electrode system including electrodes as illustrated in FIG.

1. The correspondence to the illustrated electrodes is as follows. Optional electrode 310 corresponds to electrode 11, and is the uninsulated portion of the housing of the implantable PCD. Electrode 320 corresponds to electrode 20 and is a defibrillation electrode located in the right ventricle. Electrode 311 corresponds to electrode 23, and is located in the right atrium and SVC. Electrode 318 corresponds to electrode 8 and is a defibrillation electrode located in the coronary sinus and great vein. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 310, 311, 318 and 320 are coupled to high voltage output circuit 234. High voltage output circuit 234 includes high voltage switches controlled by CV/defib control logic 230 via control bus 238. The switches within circuit 234 control which electrodes are employed and which are coupled to the positive and negative terminals of the capacitor bank including capacitors 246 and 248 during delivery of the defibrillation pulses.

Electrodes 324 and 326 are located on or in the ventricle and are coupled to R-wave sense amplifier 200. Operation of amplifier 200 is controlled by pacing circuitry 212 via control lines 201. Amplifier 200 performs functions in addition to amplification. Amplifier 200 includes a comparator that compares the input signal to a pre-selected ventricular sense threshold. A signal is generated on R-out line 202 whenever the signal sensed between electrodes 324 and 326 exceeds the ventricular sense threshold.

Electrodes 317 and 321 are located on or in the atrium and are coupled to P-wave sense amplifier 204. Operation of amplifier 204 is controlled by pacing circuitry 212 via control lines 205. Amplifier 204 includes a comparator that compares the input signal to a pre-selected atrial sense threshold, which is usually lower than the ventricular sense threshold. A signal is generated on P-out line 206 whenever the signal sensed between electrodes 317 and 321 exceeds the atrial sense threshold.

Amplifier 204 may include an adaptive filter for rejecting and/or attenuating far field R-waves. As will be described below, signals received from electrodes 317 and/or 321 may be processed by the analog adaptive filter prior to generation of a signal on P-out line 206. Because the far field R-waves are rejected and/or attenuated, the far field R-waves will not cause a signal to be generated on P-out line 206. The adaptive filter may receive an input from R-out line 202.

Switch matrix 208 is used to select which of the available electrodes are coupled to wide band (2.5–100 Hz) amplifier 210 for use in signal analysis. Signal analysis may be performed using analog circuitry, digital circuitry or a combination of both. For purposes of illustrating the invention, digital analysis will be described, but the invention is not limited to digital analysis.

Selection of electrodes is controlled by the microprocessor 224 via data/address bus 218. The selection of electrodes may be varied as desired. Signals from the electrodes selected for coupling to bandpass amplifier 210 are provided to multiplexer 220, and thereafter converted to multi-bit digital signals by analog-to-digital (A/D) converter 222, for storage in random access memory 226 under control of direct memory access circuit 228.

As will be described in more detail below, microprocessor 224 may employ digital signal analysis techniques to characterize the digitized signals stored in random access memory 226. Microprocessor 224 may also process digitized A-EGM and V-EGM signals. Processing may include filtering undesirable artifacts from the signals received from the atrium, and in particular, filtering far field R-waves from A-EGM signals with a digital adaptive filter. Further, microprocessor 224 may analyze the signals to recognize and classify the patient's heart rhythm.

The remainder of the circuitry is dedicated to the provision of cardiac pacing, cardioversion and defibrillation therapies. An exemplary apparatus comprises pacer timing/control circuitry 212, which includes programmable digital counters that control the basic time intervals associated with DDD, VVI, DVI, VDD, AAI, DDI and other modes of single and dual chamber pacing. Circuitry 212 also controls escape intervals associated with anti-tachyarrhythmia pacing in both the atrium and the ventricle, employing any of a number of anti-tachyarrhythmia pacing therapies.

Intervals defined by pacing circuitry 212 include: atrial and ventricular pacing escape intervals; the refractory periods during which sensed P-waves and R-waves are ineffective to restart timing of the escape intervals; and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by a signals on lines 202 and 206, and in accordance with the selected mode of pacing on time-out trigger generation of pacing pulses by pacer output circuitry 214 and 216, which are coupled to electrodes 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

In some circumstances, sensed far field R-waves may potentially be mistaken for P-waves in atrial depolarizations sensed by electrodes 317 and 321 (electrodes 17 and 21 in FIG. 1). Mistaking a far field R-wave for a P-wave may have an effect upon the ability accurately to detect atrial tachyarrhythmias. For example, if microprocessor 224 were to interpret a P-R interval as a P-P interval, a non-existent tachyarrhythmia may be detected. The detected P-R interval, which is shorter that the P-P interval, may be misinterpreted as more frequent atrial depolarizations than are actually taking place. The present invention rejects and/or attenuates far field R-waves, reducing the risk that a P-R interval will be interpreted as a P-P interval.

Microprocessor 224 typically operates as an interrupt-driven device, under control of a stored program in its read only memory and is responsive to interrupts from pacer timing/control circuitry 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into pacer timing and control circuitry 212. In the event that generation of a cardioversion or defibrillation pulse is required, microprocessor 224 employs an escape interval counter to control timing of such cardioversion and defibrillation pulses, as well as associated refractory periods.

In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246 and 248 via charging circuit 236, under control of high voltage charging control lines 240 and 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachyarrhythmia therapy the microprocessor then returns the device to cardiac pacing and awaits the next successive interrupt due to pacing or the occurrence of a sensed atrial or ventricular depolarization.

Delivery of the cardioversion or defibrillation pulses is accomplished by output circuit 234, under control of control circuitry 230 via control bus 238. Output circuit 234 determines whether a monophasic or biphasic pulse is delivered, the polarity of the electrodes and which electrodes are involved in delivery of the pulse. Output circuit 234 also includes high voltage switches that control whether electrodes are coupled together during delivery of the pulse. Alternatively, electrodes intended to be coupled together during the pulse may simply be permanently coupled to one another, either exterior to or interior of the device housing, and polarity may similarly be pre-set, as in some implantable defibrillators.

Mistaking a far field R-wave for a P-wave may cause microprocessor 224 to detect a non-existent tachyarrhythmia. In particular, mistaking a far field R-wave for a P-wave may cause microprocessor 224 to oversense the atrial rate. A bigeminal signal consisting of a P-wave and a far field R-wave may be interpreted as two successive P-waves. Consequently, the sensed atrial rate may be interpreted to be twice the actual rate. As a result, therapies may be applied unnecessarily and possibly to the detriment of the patient. Shock therapies such as those described above, for example, may be applied to the patient's heart to correct a condition that does not in fact exist.

In most cases, it is ill-advised to deal with far field R-waves by ignoring them. For example, analog or digital signal processing elements could be configured to ignore a portion of an A-EGM signal, such as the first few microseconds following the P-wave. While this technique would prevent detection of far field R-waves, it would also prevent detection of signals indicative of potential arrhythmias that may be occurring at the same time. Appropriate therapy might not be provided to the patient if the arrhythmias are not detected.

Figure 3:
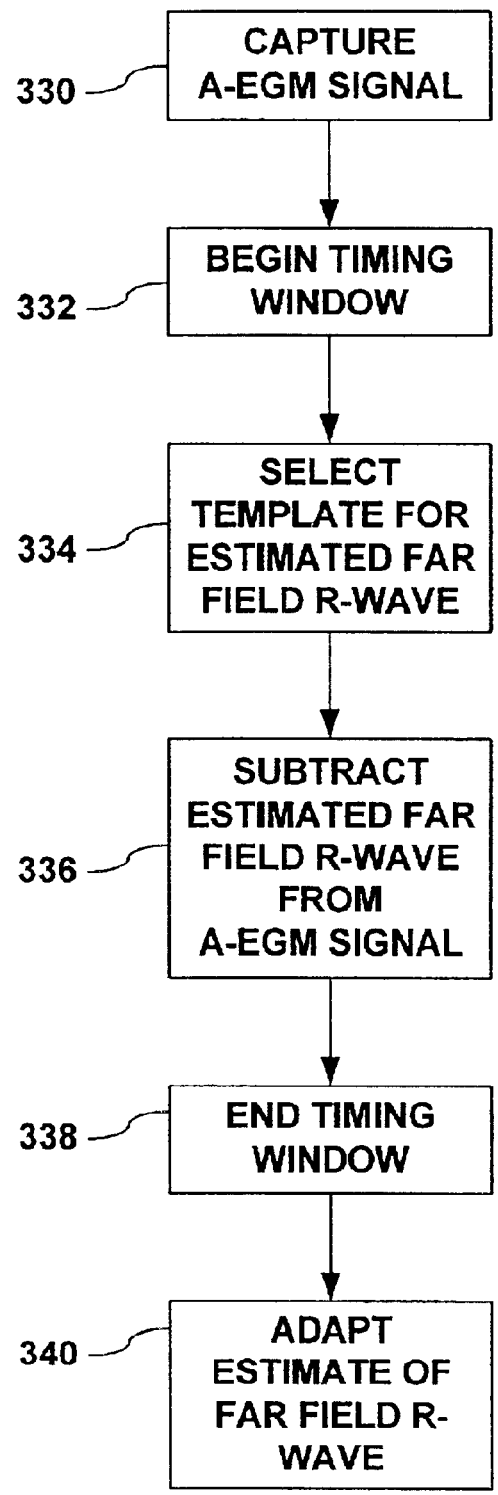
FIG. 3 is a flow diagram illustrating processing of A-EGM signals.

The present invention does not ignore far field R-waves, but seeks to reject and/or attenuate them by subtracting an estimated far field R-wave from the A-EGM signal. FIG. 3 is a flow diagram providing an overview of the technique. The A-EGM signal is captured for each cardiac cycle (330). The signal is captured in the sense that it is preserved for signal processing by analog or digital techniques.

Because a far field R-wave appears, if at all, in a brief interval of the cardiac cycle, it is not necessary to filter most of the A-EGM signal. Rather, it is more effective and economical to filter a portion of the A-EGM signal and, in particular, that portion in which the far field R-wave is likely to appear. Accordingly, a timing window begins (332), which estimates the likely interval in which the far field R-wave is likely to appear in the A-EGM signal.

A typical timing window begins about 150 ms after the P-wave and has a duration of about 200 ms. These parameters may vary from patient to patient. Although the timing window may be triggered by the P-wave or other atrioventricular event, in many patients the timing window may be triggered by the R-wave detected by the V-EGM.

A far field R-wave template, i.e., an estimate of a far field R-wave, is selected for this timing window (334). Far field R-waves may change from beat to beat, and consequently a template that accurately estimates a far field R-wave under one set of circumstances may not accurately estimate the far field R-wave under another set of circumstances. For example, the estimated far-field R-wave may be of morphology under normal sinus rhythm (NSR) conditions, of a second morphology in the case of a premature ventricular contraction (PVC) and of a third morphology in the case of a paced ventricular beat.

Different far field R-wave templates may be selected for different conditions. The selection may be a function of multiple factors. For example, the template reflecting a far field R-wave under NSR conditions may be a "default" template, and will be selected unless there is a reason to select another template. Selection of other templates may be a function of cardiac activity, such as a PVC, a bigeminal rhythm, atrial flutter or a paced beat. When a PVC is sensed, for example, the PVC template may be selected, supplanting the NSR far field R-wave template.

Template selection may also be a function of factors such as V-EGM rate, which reflects the R-R interval, or V-EGM amplitude. The timing and pattern of the A-EGM signal, the V-EGM signal or both signals may be a criterion for template selection. Template selection may also be based upon the results of a correlation analysis between the actual A-EGM signal and exemplary A-EGM signals reflecting a variety of far field R-waves.

The selected estimated far field R-wave is subtracted from the captured A-EGM signal (336), and the timing window ends (338). The difference between the original captured A-EGM signal and the estimated far field R-wave is an A-EGM signal in which the far field R-wave is attenuated, i.e., a filtered A-EGM signal. In the filtered A-EGM signal, the far field R-wave is usually significantly reduced such that the far field R-wave will not be mistaken for a P-wave.

The resulting filtered A-EGM signal may be evaluated for the effectiveness of the attenuation. Based upon the effectiveness of the attenuation, the selected far field R-wave template may be adjusted for the next cardiac cycle to improve the results (340). The cycle of monitoring and adjustment allows the far field R-wave template to adapt to changes in the morphology of the far field R-wave. Adjustment (340) may take place before the timing window ends (338).

Changes in the patient's far field R-waves are addressed in two ways. Drastic changes in far field R-waves may be addressed by template selection (334). Adjustment (338) may further refine the template to the patient's conditions.

The techniques shown in FIG. 3 may be implemented using many different analog or digital processing operations. Such processing operations may include, for example, sampling, adding, subtracting, multiplying, selecting, averaging, weighting and filtering. The processing operations may be implemented with analog circuitry, digital circuitry or a combination of analog and digital circuitry. For purposes of the following discussion, digital processing will be described in detail, and it will be assumed that most digital processing operations are performed by microprocessor 224.

Figure 4:
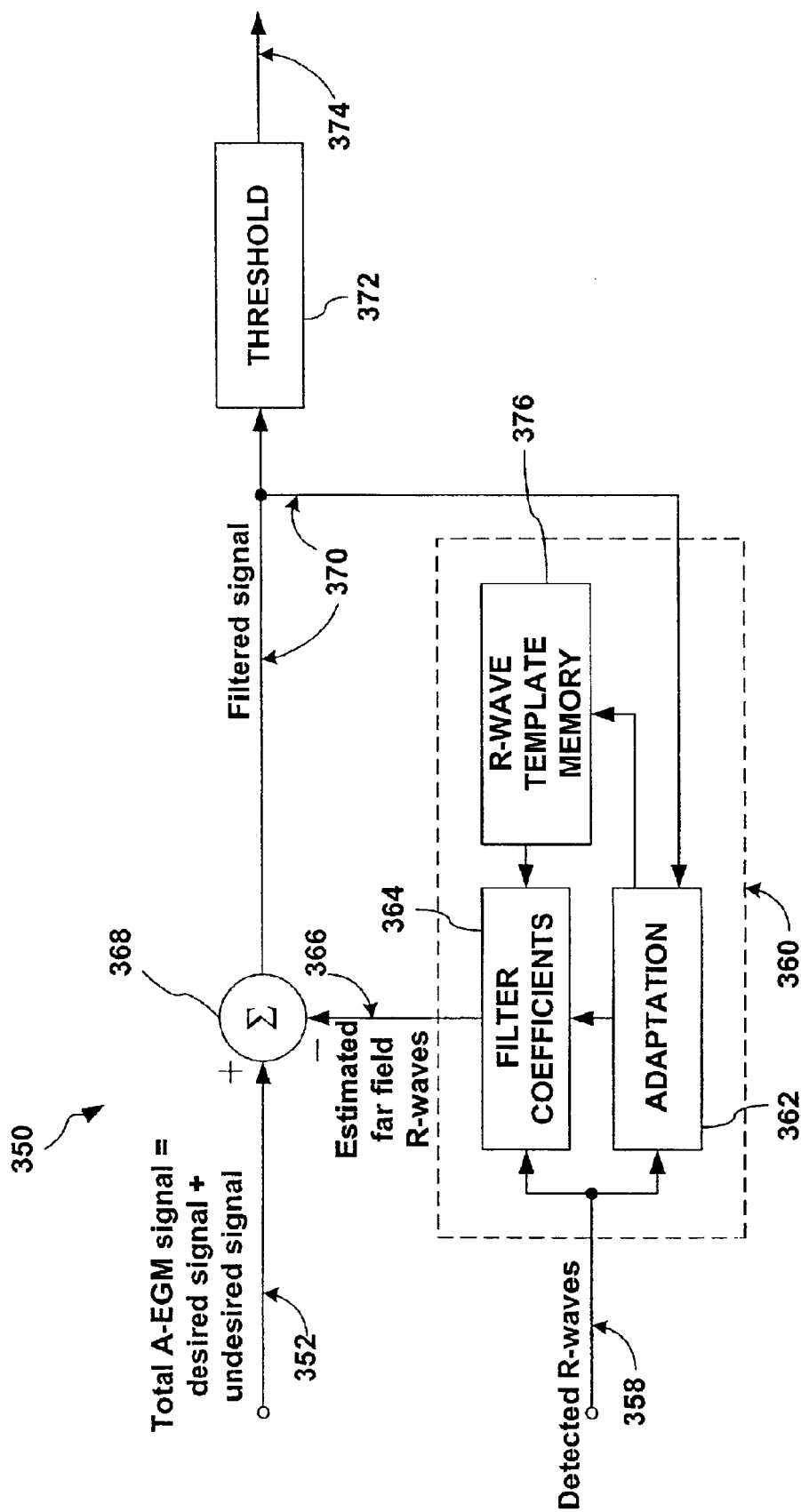
FIG. 4 is a block diagram illustrating a filter system.

FIG. 4 is a block diagram of filtering system 350 that reduces the effect of far field R-waves while also allowing atrial signals to be monitored for possible arrhythmias. Filtering system 350 may be implemented as a part of amplifier 204 in FIG. 2, or within microprocessor 224, or within a separate, dedicated subsystem not shown in FIG. 2.

One input to filtering system 350 represents A-EGM signal 352. A-EGM signal 352 may be, for example, a sampled A-EGM signal for a single cardiac cycle, digitized by A/D converter 222. A-EGM signal 352 comprises a desired signal, i.e., a signal representing atrial activity, and an undesired signal, i.e., a far field R-wave due to ventricular activity.

Another input to filtering system 350 represents R-wave 358 detected by a V-EGM. Adaptive filter 360 receives this input. In many patients, detected R-wave 358 may precede the far field R-wave, and consequently detected R-wave 358 may be used as a trigger to commence the timing window. Detected R-wave 358 is correlated to far field R-waves present in A-EGM signal 352, and provides a basis for the timing of far field R-waves and for estimating the waveforms of the undesired far field R-wave signals 366.

Filtering system 350 may include other inputs not shown in FIG. 4. For example, adaptive filter 360 may receive signal that indicates when a patient has received a stimulation with a ventricular pacing electrode. Adaptive filter 360 may also receive a signal indicative of another cardiac event, such as a PVC.

Until the timing window commences, filtering system 350 is inactive. Once the timing window commences, however, adaptive filter 360 selects a template that estimates far field R-waves 366. Estimated far field R-waves 366 are subtracted from A-EGM signal 352.

The difference between A-EGM signal 352 and estimated far field R-waves 366 is filtered A-EGM signal 370. Subtraction 368 may also include a timing adjustment, such as a delay to A-EGM signal 352 or to estimated far field R-wave 366. The timing adjustment may be introduced because A-EGM signal 352 and detected R-wave signal 358 may be detected by different sensing electrodes. Typically, A-EGM signal 352 can record a far field R-wave from about 50 ms before detected R-wave 358 to about 150 ms after detected R-wave 358. The timing adjustment allows estimated far field R-waves 366 to be subtracted 368 at the correct point in the A-EGM signal.

In a typical implementation, A-EGM signal 352 may be delayed by 5 to 20 ms. Delaying A-EGM signal 352 in turn results in a delay of filtered signal 370 and output signal 374 by 5 to 20 ms. Delays of such a short duration are usually not significant.

Following subtraction 368, the result is a filtered A-EGM signal 370 with far field R-waves attenuated. Filtered A-EGM signal 370 may be subject to further signal processing. For example, when filtered signal 370 exceeds sense threshold 372, output signal 374 may a pulse signal that marks the presence of a P-wave in the electrogram.

Filtered signal 370 is fed back to adaptive filter 360. Adaptive filter 360 includes filter coefficients 364, also called filter weights. Filter coefficients 364 may be stored in R-wave template memory 376. R-wave template memory 376 may be included in memory 226 or in another memory element or may be a separate, specially dedicated memory element. Filter coefficients 364 define the far field R-wave template, i.e., the shape of estimated far field R-wave 366, and R-wave template memory 376 may store filter coefficients for a plurality of templates.

Adaptive filter 360 includes adaptation element 362, which may be embodied within microprocessor 224 or may be a dedicated processor, such as a field-programmable gate array. Adaptation element 362 may make gross changes to the far field R-wave template, or may make minor changes to the far field R-wave template, or both.

When a substantial change is warranted, adaptation element 362 may select a template from R-wave template memory 376, thereby supplanting the previous filter coefficients 364. When a patient undergoes a stimulation from a ventricular pacing electrode, for example, a template that reflects an NSR far field R-wave may not include filter coefficients 364 that accurately reflect an estimate of the far field R-wave that results from ventricular pacing. Accordingly, adaptation element 362 may select a far field R-wave template appropriate for ventricular pacing, resulting in filter coefficients 364 that more closely reflect the actual far field R-wave.

When minor changes are warranted, adaptation element 362 may select the template used for the previous cardiac cycle, and may adjust filter coefficients 364 of that template to reflect the changes. In a typical implementation, adaptation element 362 makes minor changes to a far field R-wave template by applying a least mean square computation, to minimize the mean squared error between filtered A-EGM signal 370 and estimated far field R-wave signal 366. In other words, adaptation element 362 applies a least mean square computation to minimize the far field R-wave in the timing window of A-EGM signal 352.

Filter coefficients 364 may be adjusted by adaptation element 362 with each cardiac cycle. In this way, adaptation element 362 continually modifies adaptive filter 360 to conform to changes in the far field R-waves in A-EGM signal 352.

The morphology of the far field R-waves may change with time. Through use of feedback, adaptation element 362 adjusts filter coefficients 364 gradually to the changes in the morphology of the far field R-waves. Furthermore, adaptive filter 360 is typically triggered by detected R-wave 358 and is operative for a narrow time window for each cardiac cycle. Estimated far field R-wave signal 366, therefore, is of considerably shorter duration than a cardiac cycle.

Assume the waveforms are sampled N times and let k represent an arbitrary sample time. Let r represent the number of samples taken from the time an R-wave is detected to sampling time k. Let $X_k$ be an N×1 vector that consists entirely of zeros, except for the sample corresponding to the time the R-wave is detected, which is a 1. Let $W_k$ be the coefficient weight vector at sampling time k, and let $W_k(i)$ be the ith element of vector $W_k$ at sampling time k. The output of adaptive filter 360 at any sampling time k is:

$$\text{Estimated far field R-wave at sampling time } k = w_k(r)$$

Consequently, filtered signal 370 at sampling time k (denoted $e_k$) is equal to total A-EGM signal 352 at sampling time k minus $w_k(r)$. The coefficient weights are updated as follows:

$$W_{k+1} = W_k + (\mu \times X_k \times e_k)$$

where $\mu$ is an adaptation coefficient representing a rate of convergence. Typical adaptation coefficients may be ½, ¼, ⅛ or 1/16. Each of these adaptation coefficients is a power of two and may be realized by bit-shifting filtered signal 370 at sampling time k.

A larger adaptation coefficient results in faster adaptation and faster convergence, but may also result in greater susceptibility to noise and to irregular intermittent changes in far field R-wave morphologies. A smaller adaptation coefficient is less susceptible to noise but adapts more slowly to changes in the morphology of the far field R-waves.

The coefficient weights are further updated as follows, for i=0 to N−1, $$w_{k+1}(i) = w_k(i) + (\mu \times x_{k-1} \times e_{k-i}) \text{ for } i<r;$$

$$w_{k+1}(i) = w_k(i) + (\mu \times e_{k-i}) \text{ for } i=r;$$

$$w_{k+1}(i) = w_k(i) \text{ for all other } i.$$

The filter weights are updated such that one coefficient is updated at any sample time. When all N weights are updated, adaptive filter 360 may remain inactive until the next timing window. While inactive, adaptive filter 360 may assume a low-power configuration.

Figure 5:
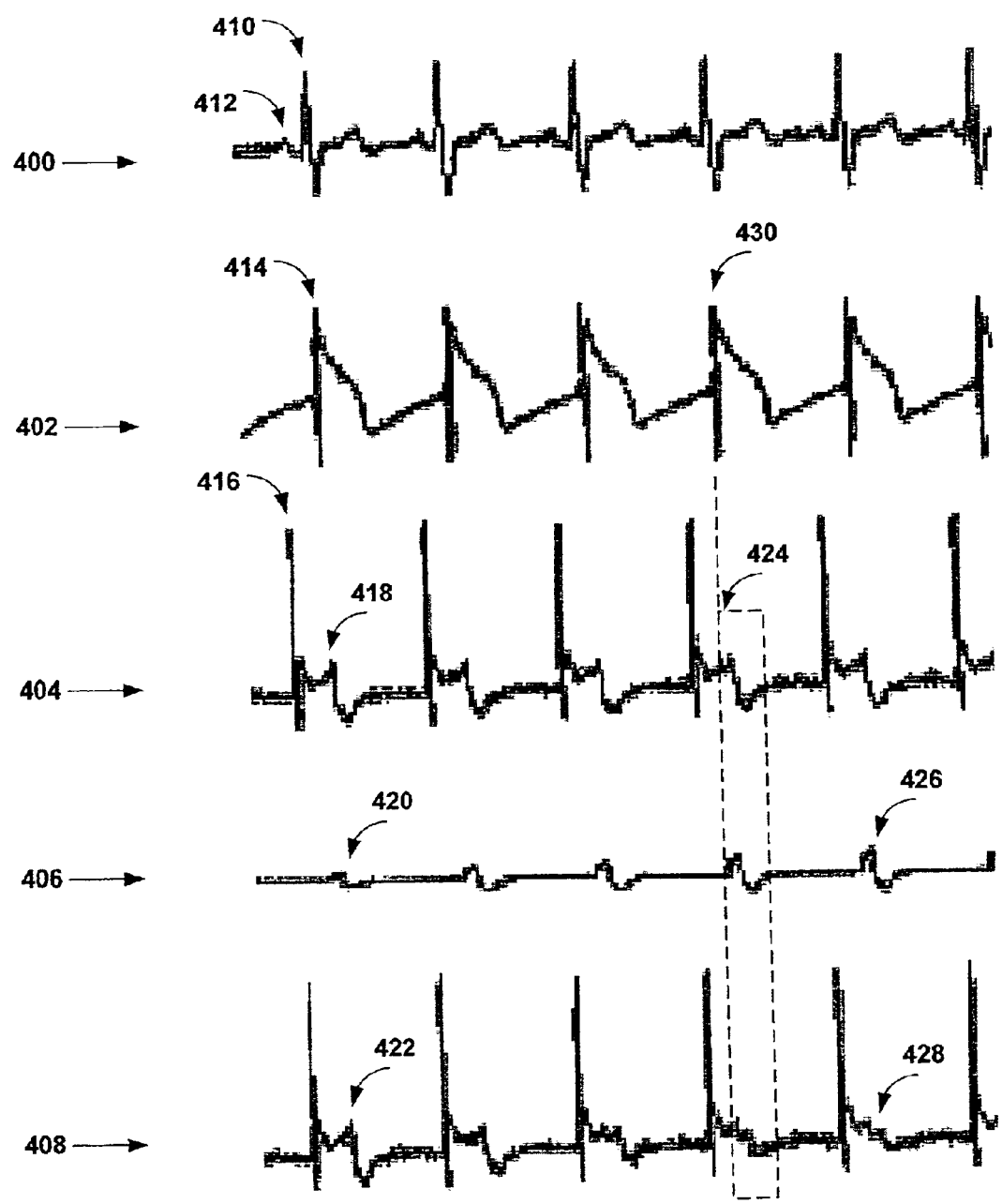
FIG. 5 is a series of cardiac waveforms, including an electrocardiogram, a V-EGM waveform, an A-EGM waveform, an estimated far field R-waves and a processed A-EGM signal.

FIG. 5 illustrates the results of application of these adaptation techniques over several cardiac cycles. FIG. 5 includes waveform 400 of a standard electrocardiogram, in which R-wave 410 is prominent, preceded by less prominent P-wave 412. As is evident from V-EGM waveform 402, R-wave 414 appears as a prominent high-amplitude wave. In A-EGM waveform 404, P-wave 416 is prominent, but far field R-wave 418 is also present. Far field R-wave 418 may exceed the sense threshold, resulting in an incorrect reading of a P-wave.

Estimated far field R-wave waveform 406 represents the output from adaptive filter 360 in FIG. 4. The difference between A-EGM waveform 404 and estimated far field R-wave waveform 406 is filtered A-EGM signal 408.

As shown in FIG. 5, estimated far field R-wave 420 is comparatively small on the first cardiac cycle, and as a result, far field R-wave 422 is not significantly attenuated in filtered A-EGM signal 408. On successive cardiac cycles, however, the magnitude of the estimated far field R-wave undergoes adaptation. By the fifth cardiac cycle, estimated far field R-wave 426 has been adapted such that after subtraction, far field R-wave 428 is significantly attenuated and less likely to exceed the sense threshold.

Notably, the duration of an estimated far field R-wave is less than a cardiac cycle. As shown in FIG. 5, an estimated far field R-wave has approximately the duration of typical window 424. Window 424 may be commenced when R-wave 430 is sensed in V-EGM waveform 402 and may end after a defined interval. As a result, the filtering affects an interval of a cardiac cycle of A-EGM waveform 404, rather than the entire cardiac cycle.

Figure 6:
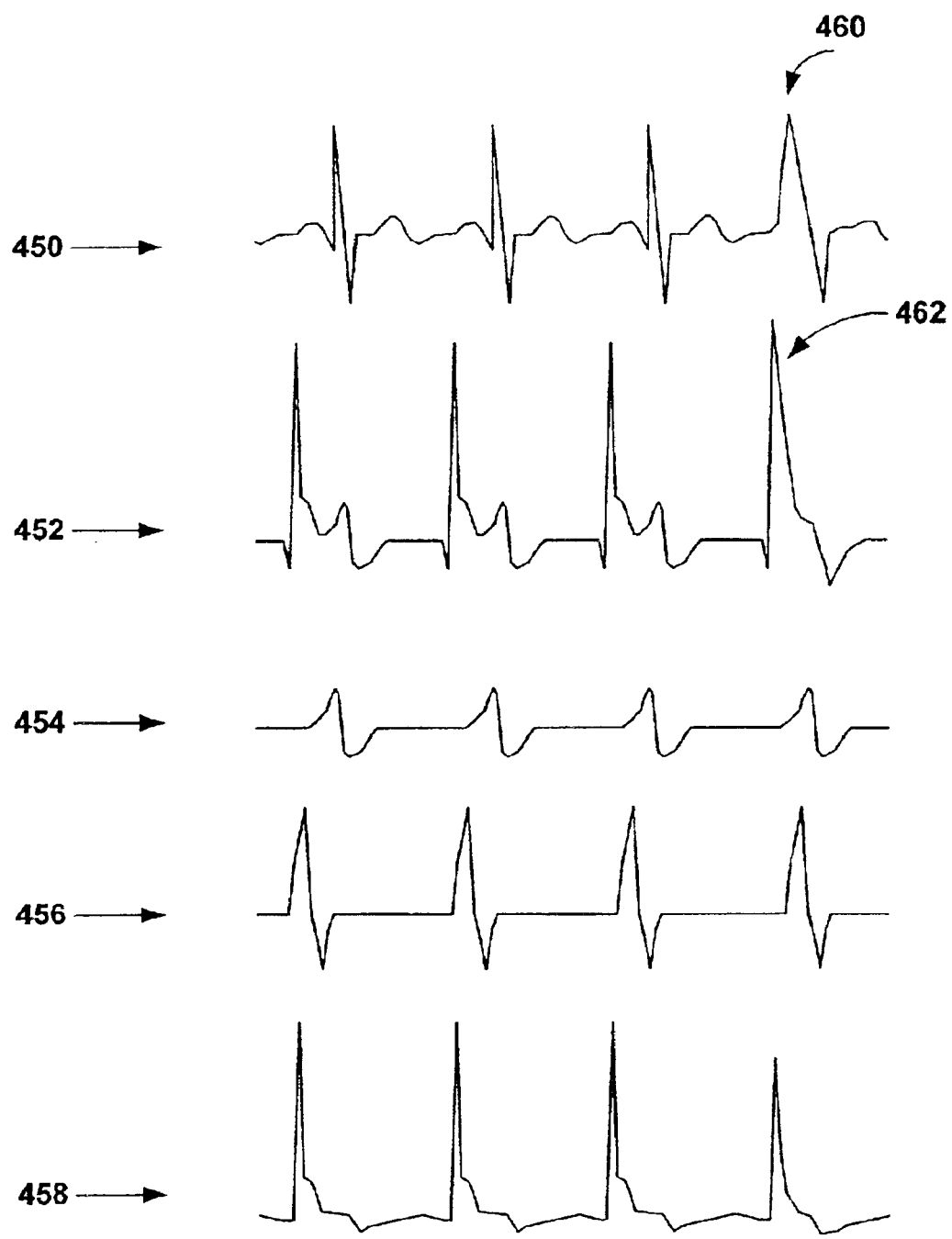
FIG. 6 is a series of cardiac waveforms, including an electrocardiogram, an A-EGM waveform, two templates estimating far field R-waves and a processed A-EGM signal.

FIG. 6, by contrast, illustrates circumstances in which the patient's far field R-wave undergoes a drastic change. Accordingly, gradual changes to filter coefficients 364 are not indicated, and adaptation element 362 supplants the coefficients by selecting a new template from R-wave template memory 376.

FIG. 6 shows four cardiac cycles of electrocardiogram signal 450, A-EGM signal 452 and filtered A-EGM signal 458. FIG. 6 also includes two far field R-wave templates 454 and 456. Far field R-wave template 454 reflects a typical far field R-wave for the patient. Far field R-wave template 456, however, reflects a far field R-wave that would be expected when the patient experiences a PVC.

The patient experiences a PVC in the fourth cardiac cycle. The PVC is evident from electrocardiogram 460, which shows the ventricle depolarizing prematurely. As a result, A-EGM signal 462 shows a change in shape due to the PVC. In particular, the far field R-wave is detected earlier than usual, and the morphology of a far field R-wave caused by a PVC is different from the morphology of a typical far field R-wave.

Adaptive filter 360 selects typical far field R-wave template 454 for the first three cardiac cycles, and subtracts template 454 from A-EGM signal 452. In the fourth cardiac cycle, however, adaptive filter 360 senses a PVC and selects template 456, which is designed to reflect the morphology of a far field R-wave caused by a PVC. By selection of the appropriate template, far field R-waves are suppressed when the patient's far field R-wave undergoes a drastic change. If the patient returns to a normal sinus rhythm on the following cardiac cycle, adaptive filter 360 may once again select typical far field R-wave template 454.

Selecting a far field R-wave template has advantages. Notably, template selection produces a more rapid response to changes in the far field R-wave than adaptive filtering alone. In addition, template selection is useful for filtering sporadic events, i.e., events such as PVC's that may not appear at regular intervals. Adaptive filtering, by contrast, tends to work well filtering regularly occurring events.

Various embodiments of the invention have been described. These embodiments are illustrative of the practice of the invention. Various modifications may be made without departing from the scope of the claims.

A-EGM and V-EGM signals may undergo additional processing, as part of filtering of far field R-waves or as part of other signal analysis. For example, A-EGM and V-EGM signals may be rectified prior to processing, and consequently the estimated far field R-wave and filtered A-EGM will be rectified as well.

Furthermore, the filtering described above is not exclusive of other signal processing techniques, and may be employed in addition to or as an alternative to other techniques for handling far field R-waves.

These and other embodiments are within the scope of the following claims.

What is claimed is:

1. A method comprising:

receiving an atrial electrogram signal as a function of electrical activity of a heart;

determining a condition corresponding to the received signal;

selecting an estimated far field R-wave for a cardiac cycle from a plurality of estimated far field R-waves in response to the determined condition; and subtracting the selected estimated far field R-wave from the atrial electrogram signal for the cardiac cycle.

2. The method of claim 1, further comprising generating a filtered atrial electrogram signal as a function of the difference between the atrial electrogram signal and the selected estimated far field R-wave.

3. The method of claim 1, further comprising:
sensing a premature ventricular contraction; and
selecting an estimated far field R-wave associated with a premature ventricular contraction.

4. The method of claim 1, further comprising:
sensing a ventricular pace; and
selecting an estimated far field R-wave associated with a ventricular pace.

5. The method of claim 1, further comprising commencing a timing window upon sensing an R-wave.

6. The method of claim 5, wherein the duration of the timing window is approximately 200 ms.

7. The method of claim 1, further comprising capturing the atrial electrogram signal.

8. The method of claim 1, further comprising converting the atrial electrogram signal to a digital atrial electrogram signal.

9. The method of claim 1, further comprising comparing the difference between the atrial electrogram signal and the selected estimated far field R-wave to a sense threshold.

10. The method of claim 1, further comprising delaying the atrial electrogram signal prior to the subtraction.

11. The method of claim 1, wherein the condition is one of a normal sinus rhythm, a premature ventricular contraction, a paced beat, a bigeminal rhythm, atrial flutter, a ventricular-EGM rate, timing and pattern of one of an atrial-EGM signal and a ventricular-EGM signal, and a correlation between an atrial-EGM signal and atrial-EGM signals associated with far field R-waves.

12. A method comprising:
generating an atrial electrogram signal as a function of electrical activity of a heart;
selecting a first estimated far field R-wave for a first cardiac cycle;
subtracting the first selected estimated far field R-wave from the atrial electrogram signal for the first cardiac cycle to generate a first filtered atrial electrogram signal;
selecting a second estimated far field R-wave for a second cardiac cycle;
subtracting the second selected estimated far field R-wave from the atrial electrogram signal for the second cardiac cycle to generate a second filtered atrial electrogram signal;
selecting the second estimated far field R-wave for a third cardiac cycle; and
adjusting the second selected estimated far field R-wave as a function of the second filtered atrial electrogram signal.

13. The method of claim 12, further comprising subtracting the adjusted second selected estimated far field R-wave from the atrial electrogram signal for the third cardiac cycle.

14. The method of claim 12, further comprising:
comparing the first filtered atrial electrogram signal to an atrial sense threshold; and
generating a P-wave sensing signal when the first filtered atrial electrogram signal exceeds the atrial sense threshold.

15. The method of claim 14, further comprising:
comparing the second filtered atrial electrogram signal to the atrial sense threshold; and
generating a P-wave sensing signal when the second filtered atrial electrogram signal exceeds the atrial sense threshold.

16. The method of claim 12, further comprising:
selecting the first estimated far field R-wave as a function of a first cardiac event; and
selecting the second estimated far field R-wave as a function of a second cardiac event.

17. A method comprising:
receiving an atrial electrogram signal as a function of electrical activity of a heart;
selecting an estimated far field R-wave for a cardiac cycle from a plurality of estimated far field R-waves;
subtracting the selected estimated far field R-wave from the atrial electrogram signal for the cardiac cycle;
sensing a premature ventricular contraction; and
selecting an estimated far field R-wave associated with a premature ventricular contraction.

18. A method comprising:
receiving an atrial electrogram signal as a function of electrical activity of a heart;
selecting an estimated far field R-wave for a cardiac cycle from a plurality of estimated far field R-waves;
subtracting the selected estimated far field R-wave from the atrial electrogram signal for the cardiac cycle;
sensing a ventricular pace; and
selecting an estimated far field R-wave associated with a ventricular pace.

19. A device comprising:
an atrial lead; and
a filter that selects an estimated far field R-wave from a plurality of estimated far field R-waves and subtracts the selected estimated far field R-wave from an atrial electrogram signal received from the atrial lead, wherein the filter receives the difference between the atrial electrogram signal and the selected estimated far field R-wave and wherein the filter generates a second estimated far field R-wave as a function of the difference.

20. A device comprising:
an atrial lead sensing electrical activity;
a microprocessor determining a condition corresponding to the sensed electrical activity; and
a filter that selects an estimated far field R-wave from a plurality of estimated far field R-waves in response to the determined condition and subtracts the selected estimated far field R-wave from an atrial electrogram signal received from the atrial lead.

21. The device of claim 20, wherein the difference between the atrial electrogram signal and the selected far field R-wave comprises a filtered atrial electrogram signal, the device further comprising a comparator that compares the filtered atrial electrogram signal to a pre-selected atrial sense threshold and generates an atrial sense signal when the filtered atrial electrogram signal exceeds the atrial sense threshold.

22. The device of claim 20, wherein the filter receives the difference between the atrial electrogram signal and the selected estimated far field R-wave and wherein the filter generates a second estimated far field R-wave as a function of the difference.

23. The device of claim 20, further comprising memory that stores a plurality of estimated far field R-waves.

24. The device of claim 20, further comprising:
a ventricular lead; and
a comparator that compares a ventricular signal received from the ventricular lead to a pre-selected ventricular sense threshold and generates a ventricular sense signal when the ventricular signal exceeds the ventricular sense threshold.

25. The method of claim 20, wherein the condition is one of a normal sinus rhythm, a premature ventricular contraction, a paced beat, a bigeminal rhythm, atrial flutter, a ventricular-EGM rate, timing and pattern of one of an atrial-EGM signal end a ventricular-EGM signal, and a correlation between an atrial-EGM signal and atrial-EGM signals associated with far field R-waves.

* * * * *